United States Patent
Chen et al.

(10) Patent No.: US 9,267,927 B2
(45) Date of Patent: Feb. 23, 2016

(54) ROBUST AND LOW BACKPRESSURE ON-COLUMN TUNNELED FRIT FOR NANO-UPLC-MS APPLICATIONS

(75) Inventors: Chao-Jung Chen, Dali (TW); Mei-Chun Tseng, Taipei (TW); Yet-Ran Chen, Taipei (TW)

(73) Assignee: Academia Sinica, Taipei (TW)

(*) Notice: Subject to any disclaimer, the term of this patent is extended or adjusted under 35 U.S.C. 154(b) by 751 days.

(21) Appl. No.: 13/112,519

(22) Filed: May 20, 2011

(65) Prior Publication Data

US 2011/0284466 A1  Nov. 24, 2011

Related U.S. Application Data

(60) Provisional application No. 61/347,133, filed on May 21, 2010.

(51) Int. Cl.
*G01N 30/60* (2006.01)
*B01D 15/22* (2006.01)

(52) U.S. Cl.
CPC .............. *G01N 30/603* (2013.01); *B01D 15/22* (2013.01); *G01N 30/6078* (2013.01)

(58) Field of Classification Search
CPC ... G01N 30/603; G01N 30/6078; B01D 15/22
USPC ................................ 210/635, 656, 659, 198.2
See application file for complete search history.

(56) References Cited

U.S. PATENT DOCUMENTS

| | | | |
|---|---|---|---|
| 4,469,597 A * | 9/1984 | Mott | 210/198.2 |
| 4,732,687 A * | 3/1988 | Muller et al. | 210/656 |
| 4,765,890 A * | 8/1988 | Tehrani et al. | 210/198.2 |
| 6,136,187 A * | 10/2000 | Zare et al. | 210/198.2 |
| 6,210,570 B1 * | 4/2001 | Holloway | 210/198.2 |
| 6,758,966 B2 * | 7/2004 | Myers | 210/198.2 |
| 7,316,779 B2 * | 1/2008 | Pressman et al. | 210/416.1 |
| 7,418,977 B2 * | 9/2008 | Ducree et al. | 137/825 |

(Continued)

FOREIGN PATENT DOCUMENTS

WO  WO-2009/860092 A1  7/2009

OTHER PUBLICATIONS

Tan, F. et al., "A simple and efficient frit preparation method for one-end tapered-fused silica-packed capillary columns in nano-LC-ESI MS." *Proteomics* 10: 1-4 (2010).

(Continued)

*Primary Examiner* — Ernest G Therkorn
(74) *Attorney, Agent, or Firm* — Drinker Biddle & Reath LLP

(57) ABSTRACT

A durable on-column tunneled frit was developed for use in nanoflow UPLC systems. The frit was tunneled during sol-gel reaction. The tunneled-frit fabrication process is easy and reproducible in terms of back pressure and durability. This design creates low backpressure with high liquid flow, which is suitable for the nanoflowUPLC application. A short packing (2 cm C18 particle) tunneled-frit column was demonstrated to sustain 10,000 psi continuous liquid flow for over one week without any particle leakage or pressure instability. The tunneled-frit was also successfully applied to the fabrication of nanoUPLC trapping and analytical column system. It was demonstrated to have high separation efficiency and sensitivity for the analysis of tryptic peptides as well as improved detection sensitivity for phosphopeptide analysis.

8 Claims, 7 Drawing Sheets

Flow chart of the preparation of the tunnel frit

(56) References Cited

U.S. PATENT DOCUMENTS

| | | | |
|---|---|---|---|
| 2004/0200776 A1* | 10/2004 | Ivanov et al. | 210/656 |
| 2004/0238447 A1 | 12/2004 | Cheong | |
| 2006/0032816 A1* | 2/2006 | Marcus et al. | 210/634 |
| 2006/0144770 A1* | 7/2006 | Granger et al. | 210/198.2 |
| 2006/0201881 A1* | 9/2006 | Marcus et al. | 210/638 |
| 2007/0295663 A1* | 12/2007 | Iraneta et al. | 210/656 |
| 2008/0190830 A1* | 8/2008 | Maltezos et al. | 210/198.2 |
| 2011/0114549 A1* | 5/2011 | Yin et al. | 210/198.2 |
| 2011/0139718 A1* | 6/2011 | Snyder | 210/656 |
| 2012/0031820 A1* | 2/2012 | Reinhardt | 210/85 |
| 2013/0001145 A1* | 1/2013 | Yin et al. | 210/198.2 |

OTHER PUBLICATIONS

Wang, L. et al., "A simple and inexpensive on-column frit fabrication method for fused-silica capillaries for increased capacity and versatility in LC-MS/MS applications." *Proteomics* 8: 1758-1761 (2008).

Wang, F., et al., "Integration of monolithic frit into the particulate capillary (IMFPC) column in shotgun proteome analysis." *Analytica Chemica Acta* 652: 324-330 (2009).

Schmid, M. et al., "Preparation of on-column Frits in Packed Fused Silica Capillaries by Sol-Gel Technology." *J. High Resol. Chromatogr.* 22(8): 438-442 (1999).

Zhang, X. et al., "Single step on-column frit for making capillary high-perforomance liquid chromatography using sol-gel technology." *Journal of Chromatography A*, 910, 13-18 (2001).

Behnke, B. et al., "Evaluation of the parameters determining the performance of electrochromatography in packed capillary columns." *Journal of Chromatography A*, 716, 207-213 (1995).

Wang, H. et al., "Magnetically immobilized frits for the preparation of packed columns used in capillary electrochromatography." *Journal of Chromatography A*, 1216, 5882-5887 (2009).

* cited by examiner

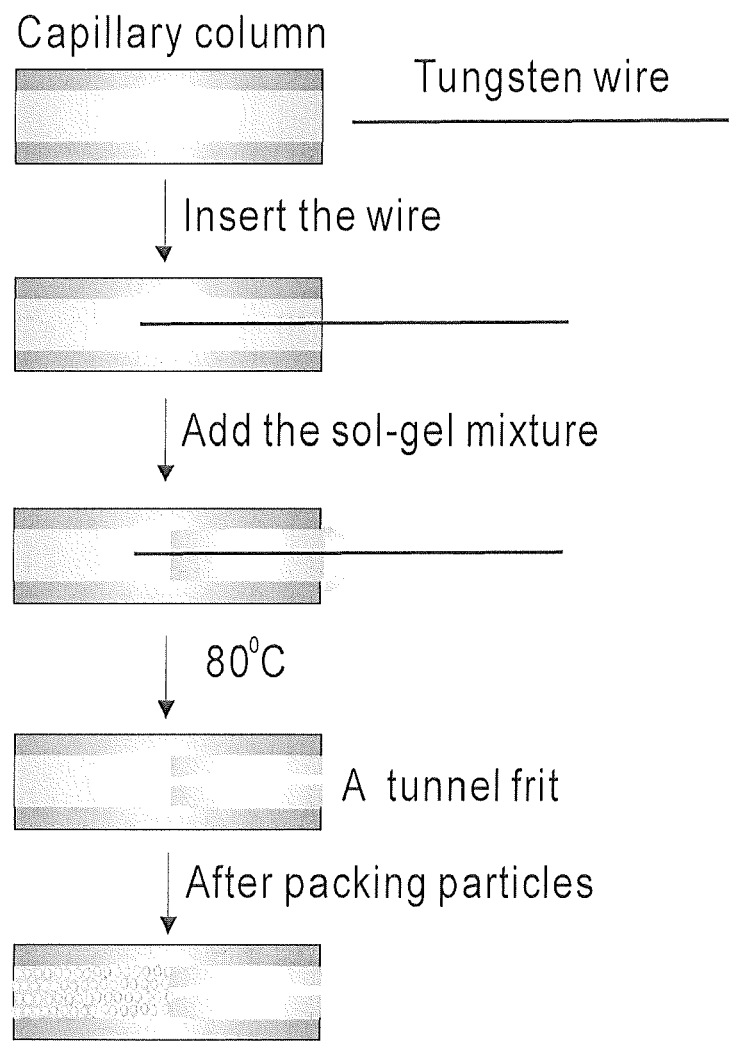
Figure 1. Flow chart of the preparation of the tunnel frit (a)
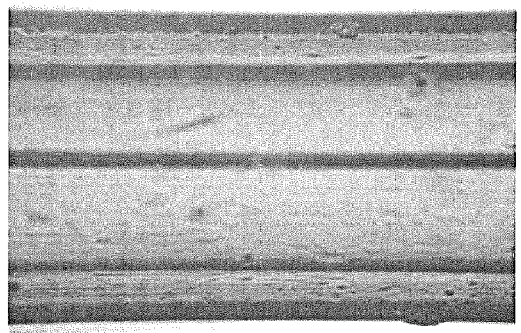
(b)
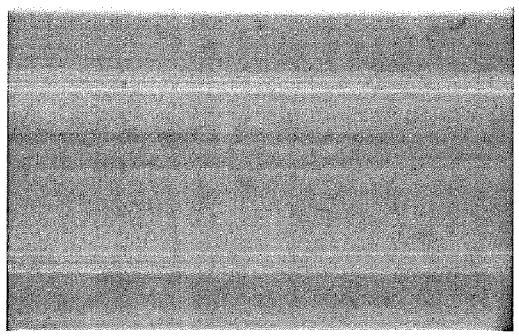
(c)
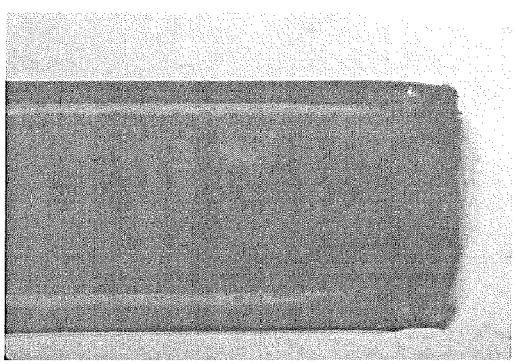
Figure 2. Photography of microscope. (a) The tungsten wire (18 μm) embedded by the sol-gel solution in the capillary column (180 μm id, 365 μm od). (b) The tunnel formation after sol-gel reaction. (c) the outlet end of the packed column.

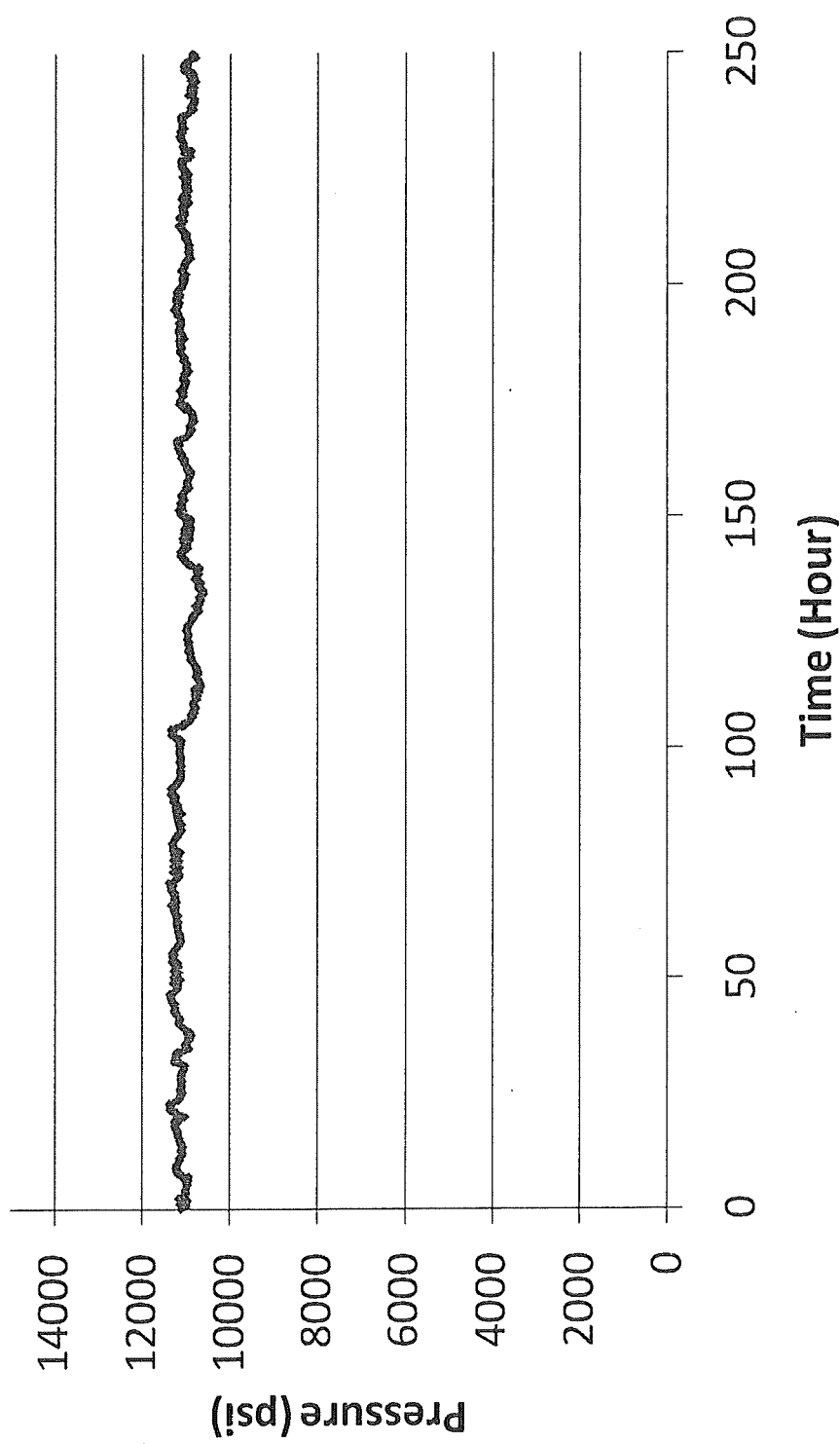
Figure 3. Long-term test of the stability of the tunnel-frit trap column under ultra high pumping pressure

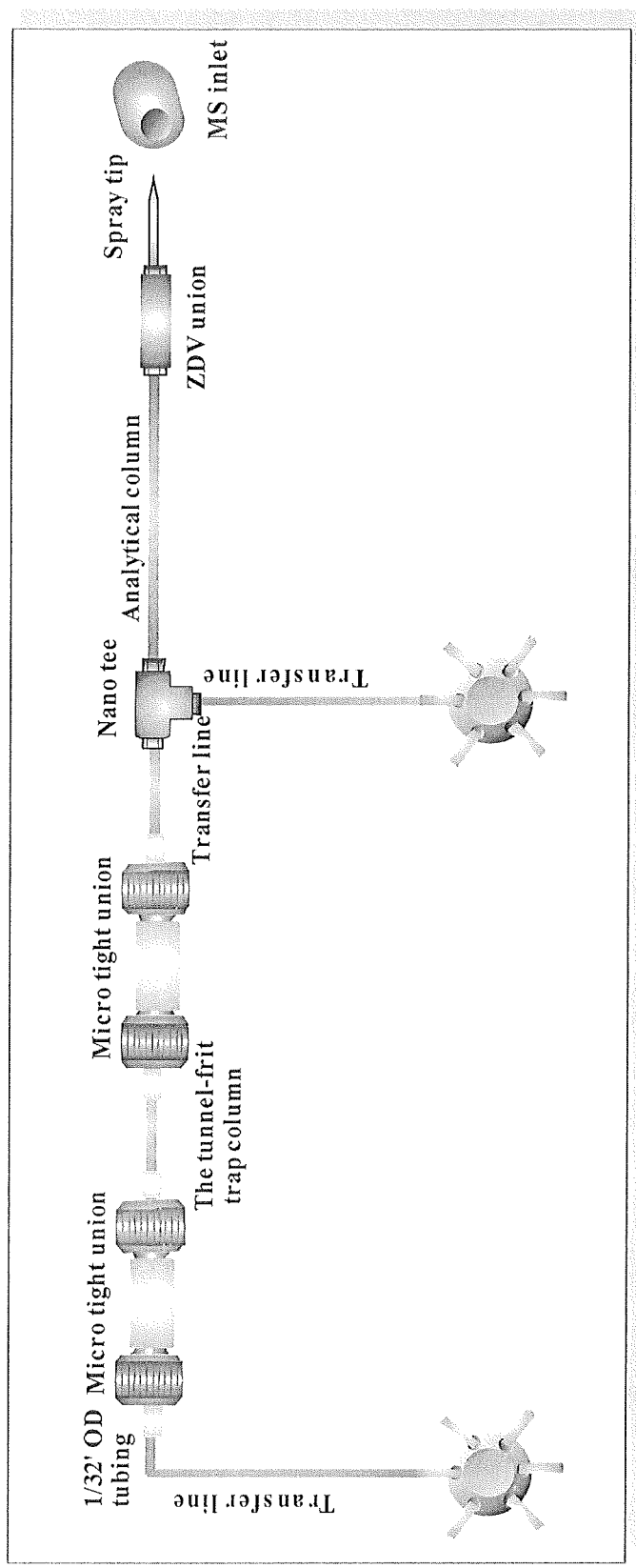
Figure 4. Schemes of the tunnel-frit trap column for nanoUPLC-MS system

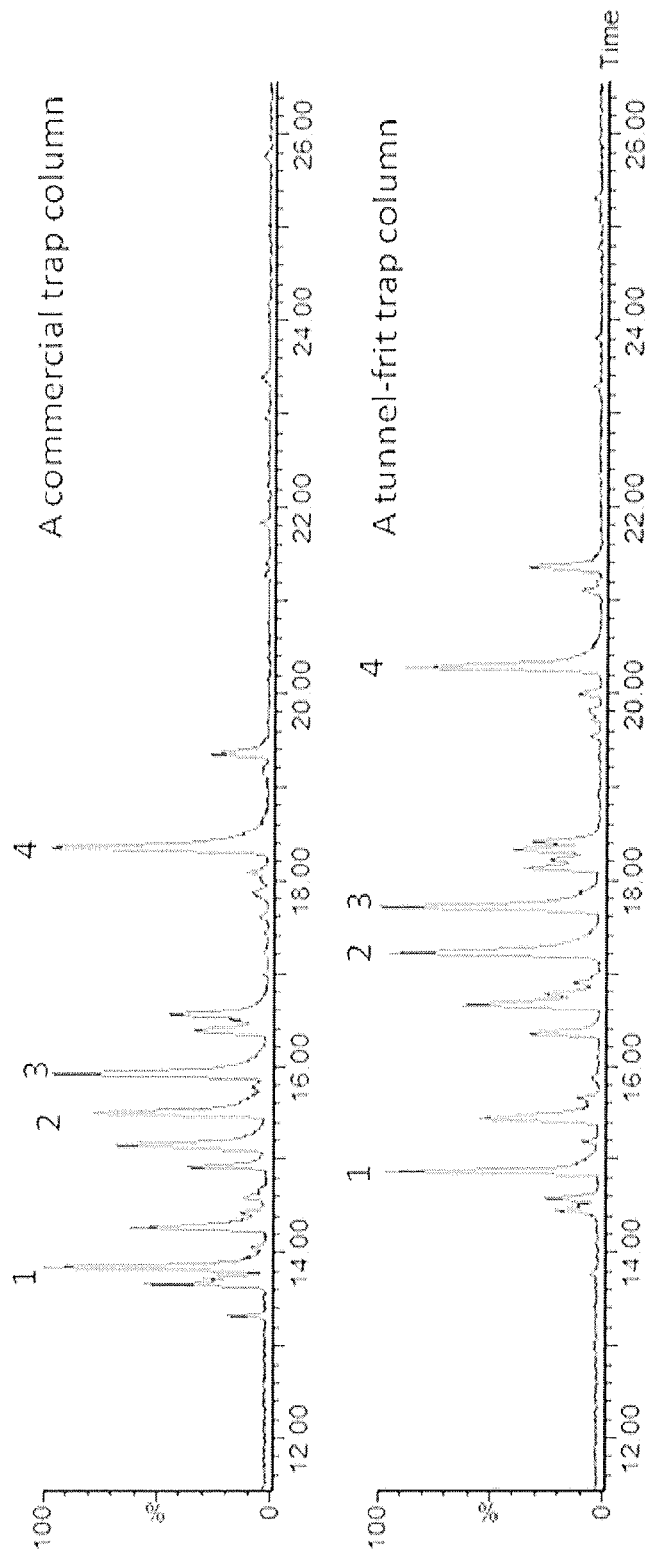
Figure 5. The Base peak chromatograms of the enolase digests (50 fmol) from nanoUPLC-MS. (a) A commercial trap column or (b) A tunnel-frit trap column was used separately on-line prior to the commercial analytical column.

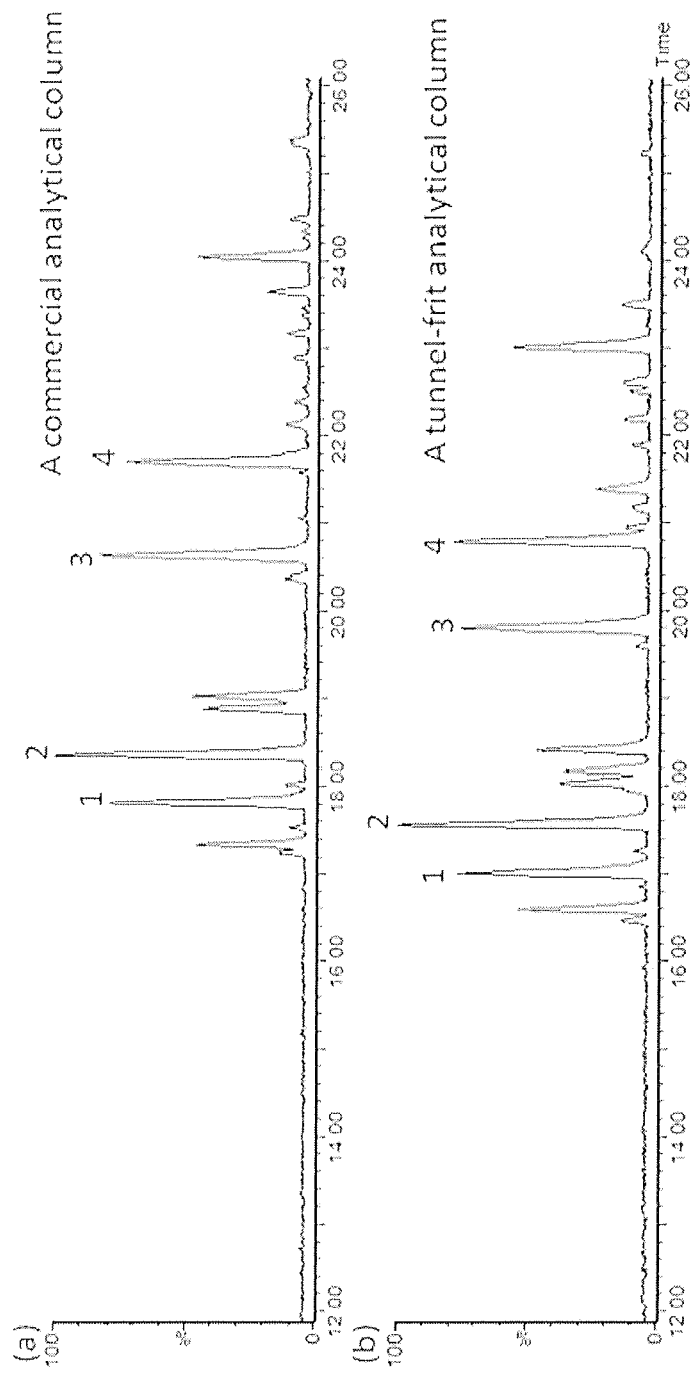
Figure 6. The Base peak chromatograms of the enolase digests (50 fmol) from (a) the commercial analytical column and (b) the tunnel-frit analytical system.

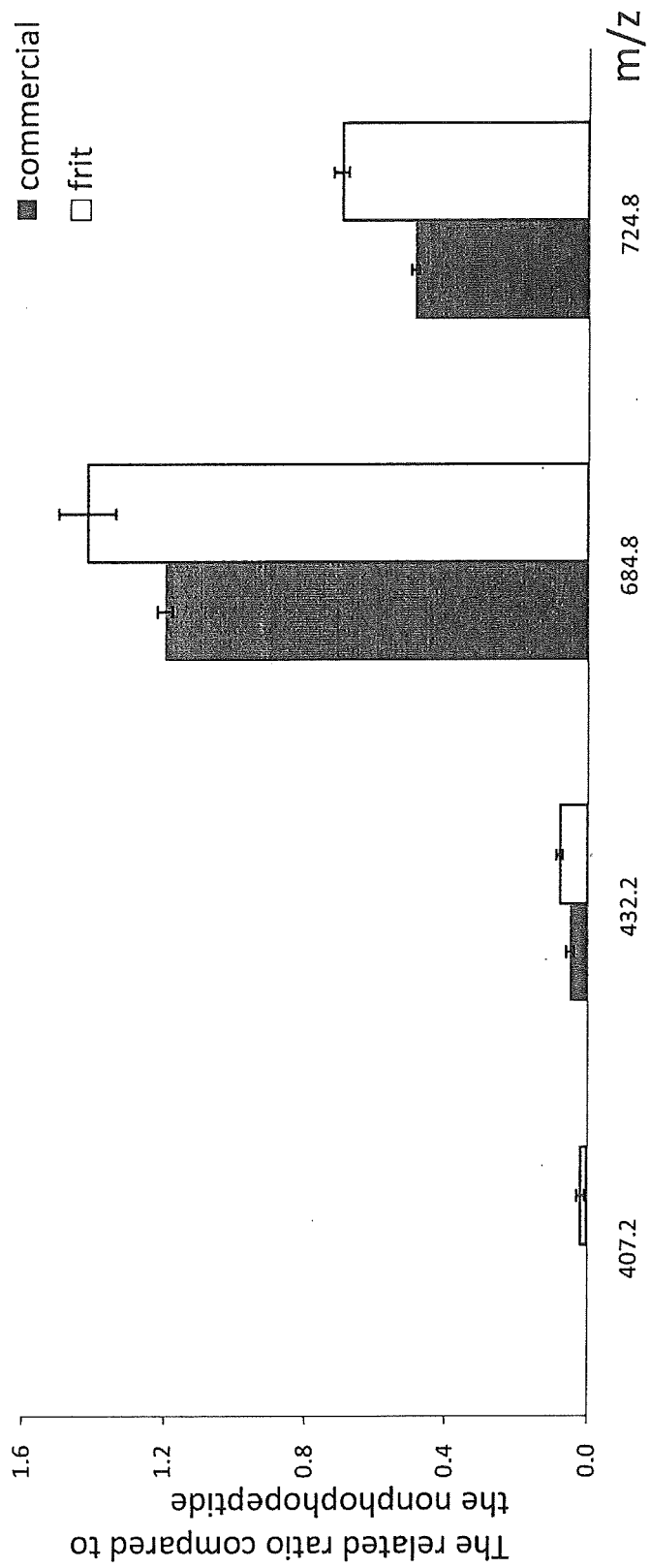
Figure 7. The comparison of four synthetic phosphopeptides signals between the commercial and the tunneled frit trap column. The relative ratio of each phosphopeptide was obtained in comparison with the nonphosphopeptide signal (643.9 m/z) acted as an internal quantitative peak.

ROBUST AND LOW BACKPRESSURE ON-COLUMN TUNNELED FRIT FOR NANO-UPLC-MS APPLICATIONS

CROSS-REFERENCE TO RELATED APPLICATIONS

Priority is claimed to U.S. Provisional Patent Application Ser. No. 61/347,133, filed on May 21, 2010, the disclosure of which is incorporated herein by reference in its entirety.

BACKGROUND

An emerging development in proteomics has provided great opportunities for biomarker discovery, drug development, and the like. Currently LC-MS has become one of the major platforms for protein identification. To date the development of new LC-MS technology is widely applied to comprehensive proteomic studies. In combination with protein fractionation, isotopic labeling and LC-MS, large amounts of protein can be identified and quantified in a short period of time. In LC-MS high resolution and high sensitivity LC separation is the determining factor for comprehensive qualitative and quantitative proteomics studies. The fused-silica capillary LC column is an essential component in the LC-MS based proteomic approach since it can provide high resolution separation of peptides with high sensitivity.

A large variety of commercial stationary phases are employed in capillary-based LC-MS systems for proteomics applications. To retain the stationary phase inside the column, tapered tip and fit designs are commonly used. In tapered tip designs, one end of the column is tapered to have 10~20 um inside diameter to provide a "keystone" effect to retain particles. The fabrication of the tapered tip capillary is simple and has minimized the post-column dead volume, thus reducing the effect of band broadening due to the longitudinal diffusion. However, once the tip is broken or contaminated, after a period of time the whole column has to be replaced with a new one to maintain the stable and sensitive ionization efficiency. In addition, the tapered tip cannot be applied to the fabrication of trapping column.

Columns containing frits to retain packings have significant benefit for both packed analytical and trap columns. In frit designs retaining frits are readily formed and fixed to the walls of a fused silica capillary by the sol-gel reaction or the sinter of a small area of silica gel or porous silica-based sorbents. A packed column with a frit at one end can be used over and over for a long time and may be re-used with new packing materials.

Trap columns are important in the LC-MS system. To concentrate and desalt a sample for higher sensitivity analysis, a trap column is often used upstream of an analytical column in nano-LC-MS systems. Unfortunately, the trap column can often be blocked by un-removed gel species or particles from sample solutions after batch analyses or it can lose the concentration factor after numerous sample analyses. Hence trap columns for nano-LC systems need to be changed frequently to sustain the original performance, and, therefore, trap columns can become an expensive cost item in a proteomics lab that routinely runs protein samples. To manufacture the trap columns or analytical columns, frit preparation methods are often the key point for the success of packed columns.

To date, many methods have been provided to improve the frit preparation. Unfortunately, the frit fabrication is not highly reproducible, leading to variations in column performance. In addition, capillaries are fragile at the position of the frit since the polyimide coating is often removed during frit fabrication (http://parteq.technologypublisher.com/technology/4510 Multi-Channel Optical Fiber as a Frit.). Recently, tapered tips or tapered tips with sintered fits (Proteomics 2010, 10, 1-4: A simple and efficient frit preparation method for one end tapered-fused silica-packed capillary columns in nano-LC-ESI MS) have been used instead of conventional frits to retain the stationary phase in the column; and also directly used as an electro-sprayer in LC-MS. However, the frequent clogging, breaking and contamination of the tip can cause the replacement of the entire packed column and therefore limits the use of the packed column with tapered tip. Moreover, because of the fragile nature and unfit size for the fitting, the tapered packed columns are not adequate to be used as trap columns.

To retain the polyimide coating and be adequate for trap columns, various sol-gel techniques for on-column fit preparation have been reported (J. High Resol Chro, 1999, 22, 438: AC 2003, 75, 4292). More recently, by dipping the sol-gel solution to a capillary column with dry Si resins inside, a simple low backpressure and inexpensive on-column fit fabrication method has been developed. However, the frit thus formed can often be flushed out during the application of high pressure. An increase of the frit strength by increasing the capillary action time of the sol-gel solution in the packed end can results in extremely high backpressure of frits which is not suitable for high pressure LC applications.

In nano-LC-MS or nanoUPLC-MS systems, because of the use of 3 μm or 1.7 μm 100 Å particles, the resulting backpressure can be extremely high and range from 5000 to 9000 psi. To manufacture the trap column for such high pressure systems, the trap column is crucial to have certain characteristics. First, because of ultra high pressure supply, the polyimide coating on the column end has to be maintained to prevent the column from breaking. In addition, the frit needs high mechanical strength for ultra high pressure resistance. Moreover, low back pressure of the frit can prevent additional pressure which may result in overpressure of the pumps during analysis.

BRIEF DESCRIPTION OF THE INVENTION

According to the present invention, we provide method and means for preparation of new and highly reproducible, high mechanical strength and low backpressure tunneled frits for packed columns. Trap columns or analytical columns containing tunneled frits of the present invention are employed in liquid chromatography including ultra high pressure systems (UP-LC) and in capillary electrophoresis (CEC) systems to separate and resolve a wide variety of proteins.

In one aspect, the invention relates to a durable capillary column suitable for use in a nanoflow UP-LC system containing a tunneled frit at one end thereof. The tunneled frit allows the development of relatively low back-pressure and serves to retain the column packing. Preferably, the frit is formed in place by curing of a suitable sol-gel mixture containing silica or other suitable polymerizable material to form a hard, dense frit bonded to the capillary column and having a tunnel communicating from inside to outside the column. A wire of suitable material is employed to produce the tunnel which communicates from inside to outside of the capillary column; and the wire is withdrawn following fabrication. Preferably, a tungsten wire having a range of diameters between about 15 μm and 25 μm is employed to create the tunnel. The tunnel diameter is relatively small compared to the diameter of the frit and preferably the ratio of tunnel diameter to frit diameter is between about 0.070 to about 0.080 and about 0.25 and about 0.35. In operation, the trap or analytical columns in combination with tunneled frits can withstand up to about 12,000 psi pressure for microflow and nanoflow LC separations.

In another aspect of the present invention, we provide a method of making durable capillary columns suitable for use in nanoflow or microflow LC systems. In general, any polymerization or sintering method and materials can be employed to make a frit with a tunnel or hole where the id (inside diameter) of the tunnel is smaller than the id of the column; and the frit can retain particles or packing inside the column. Accordingly, a suitable wire is inserted at one end of a capillary column. A suitable sol-gel is reacted or polymerized around the wire so as to fill the end of and bond to the capillary tube. The wire is then removed to create a tunnel communicating from inside to outside the capillary tube, hence the tunneled frit. The frit can be formed from any suitable polymer or sintering material. Preferably sol-gel solutions are employed including inorganic resins and prepolymers and other suitable materials including alkoxides in solution which undergo well known polymerization reactions which when cured produce dense silica glass or polymer. Tungsten wire, for example, is able to retain its shape and hence form a suitable tunnel in the frit when the wire is withdrawn from the frit. The use of other wires having properties similar to tungsten is within the present invention.

The tunneled frit formed at an end of the capillary column is preferably cured at a moderately elevated temperature, preferably between about 50-90 and most preferably between about 50-70 degrees centigrade for a few minutes (about 10-60 minutes) until it is set. Then the tunneled fit is heat treated at an elevated temperature preferably between about 50 and about 120 and most preferably between about 75 and about 100 degrees centigrade for about 4 to about 50 hours as needed to completely cure the fit.

In practice, it has been found that tunneled frits made according to the present invention are highly useful in UPLC systems up to about 12,000 psi. They are durable and may be used over and over.

In yet another aspect of the present invention, we provide a method of separating peptides which comprises passing a peptide containing material at an elevated pressure through a packed capillary column where the packing is retained and low back-pressure is maintained by a tunneled frit situated at one end of the column. The various fractions recovered are analyzed according to known methods.

In yet another preferred aspect, we have discovered that the use of a non-metallic frit exhibits improved phosphopeptide detection sensitivity compared to metallic frits of the prior art.

In still a further aspect of the present invention, we provide a system which comprises at least one capillary column employed as a trap and at least one capillary column employed as an analytical separation column, wherein one or both of said columns contain tunneled frits at one end thereof.

BRIEF DESCRIPTION OF THE DRAWINGS

FIG. 1. Flow chart of the preparation of the tunneled-frit.
FIG. 2. Photomicrographs of the tunneled frit: (a) The tungsten wire (18 μm) embedded by the sol-gel solution in the capillary column (180 μm id, 365 μm od); (b) The tunnel formation after sol-gel reaction; and (c) the outlet end of the packed column.
FIG. 3. Long-term test of the stability of the tunneled-frit trap column under high pumping pressure.
FIG. 4. Scheme including a tunneled-frit trap column for a nano-UPLC-MS system.
FIG. 5. Base peak chromatograms of enolase digests (50 fmol) from nano-UPLC-MS. A commercial trap column or a tunneled-frit trap column was used separately on-line upstream of the commercial analytical column.
FIG. 6. Base peak chromatograms of the enolase digests (50 fmol) from nano-UPLC-MS. Various tunneled-frit lengths of the trap column were studied.
FIG. 7. The comparison of four synthetic phosphopeptide signals between the commercial and the tunneled frit trap column. The relative ratio of each phosphopeptide was obtained in comparison with the non-phosphopeptide signal (643.9 m/z) and acted as an internal quantitative peak.

DETAILED DESCRIPTION OF THE INVENTION

Materials Employed in the Examples Set Forth Below

Formamide was purchased from RDH Chemicals (Poole, UK). Potassium silicate was purchased from PQ Corporation (Valley Forge, Pa.). For LC-MS analysis, the acetonitrile (ACN) with 0.1% formic acid (FA) and water with 0.1% formic acid (LC-MS grade, J. T. Baker, Phillipsburg, N.J.) were used as the mobile phase. Deionized water (18.1 MΩ·cm resistivity) from a Milli-Q system (Millipore, Bedford, Mass.) was used throughout this work.

Preparation of Tunneled-Frit Packed Columns

A flow chart of fabrication of a tunneled-frit is shown in FIG. 1. For making a trap column, an 18 μm tungsten wire (W337, Scientific instrument service, SIS, NJ) was inserted about 5 mm into one end of the capillary column (8-10 cm, 365 μm od, 180 μm id). A 15 μm tungsten wire was used for making an analytical column (35 cm, 365 μm od, 75 μm id, Polymicro Technologies, Phoenix, Ariz.). A mixture of 170 μL potassium silicate and 20 μL formamide was vortexed for 1 min. A 2 μL of the resulting sol-gel mixture was dipped on the end of the capillary column. By capillary action, the sol-gel solution moved into the column with the wire inserted (FIG. 2a). Care should be taken that the distance that the sol-gel solution moves into the column is not longer than the inserted tungsten wire. If the tunnel is sealed, the backpressure will rise enormously. After the sol-gel formation and incubation at 60° C. for 20~30 min, a clear tunnel (about 20 μm) was clearly present inside the frit (FIG. 2b). The tungsten wire had to be pulled out of the column before incubation at 80° C. for overnight. The resulting column with the tunneled-frit was connected to a pump to establish a flow rate of 0.1 ml/min MeOH. The frit length can be calculated by the arisen pressure or by observation under the microscope; and the frit can be cut and ground to have the required length (FIG. 2c).

The tunneled-frit packed column was then mounted on a homemade pressure vessel that served as a packing reservoir. A slurry of 2 mg of 5 μm stationary phase (Symmetry C18, 5 μm, Waters, Milford, Mass.) for trap columns in 1 mL of methanol or 2 mg of 5 μm stationary phase (Nucleosil C18, 5 μm, 100 Å, MACHEREY-NAGEL GmbH & Co KG, Düren, Germany) and another slurry (BEH C18, 1.7 μm, 75 μm×250 mm, Waters, Milford, Mass.) for analytical columns in 1 mL of methanol were sonicated for 5 minutes to prevent aggregation of particles and they were subsequently transferred into the reservoir. The pressure vessel was connected to a nitrogen cylinder. Once high-pressure nitrogen (1000 psi for analytical columns, 300 psi for trap columns) was provided, the ODS particles were pumped into the capillary and retained in the column. After packing to a specified length (about 2 cm for trap columns, about 25 cm for analytical columns), the packed column was removed from the packing reservoir and was ready for further use.

Nano-UPLC-MS Analysis

LC-MS was performed with a nanoflow LC system (nanoACQUITY UPLC, Waters, Millford, Mass.) coupled to a hybrid Q-TOF mass spectrometer (Synapt HDMS, Waters, Manchester, U.K.). Samples were injected into a commercial trap column (Symmetry C18, 5 µm, 180 µm×20 mm, Waters, Milford, Mass.) and into the tunneled-frit trap column, and separated online with a reverse-phase (BEH C18, 1.7 µm, 75 µm×250 mm, Waters, Milford, Mass.) analytical column or a tunneled-frit analytical column (BEH C18, 1.7 µm, 75 µm×250 mm) at the flow rate of 300 nl/min using a 23 min 12-80% acetonitrile/water gradient for tryptic enolase.

Observations Related to the Tunneled Frits

According to the capillary ID, the tunnel diameter should be considered to create a "Keystone" effect during the column packing. For the capillary ID >75 µm (normally for trap columns), the use of 18 µm wires to create 18 µm tunnel is required. For the capillary with ID <75 µm id (normally for analytical column), the use of 15 µm instead of 18 um tungsten wire is recommended, because the 15 µm tunnel can produce more significant "keystone" effect for the smaller id capillary. The backpressure measured by the about 2 mm tunneled-frit for the 0.1 ml/min MeOH was found to have a reproducible value of 120 to about 160 psi (n=5) which is similar to the backpressure created between the 20 µm id (about 116 psi) and 15 µm id (about 160 psi) capillary column. It illustrated that the tunnel size inside the frit is determined by the wire and the measured value from tunneled-frit columns can also be used to calculate the frit length. Additionally, the frit length can be determined by cutting the outlet end and by grinding to have a flat end to reduce the dead volume resulting in peak broadening during the column connection. Except for the final incubation time in oven, the fabrication process of the tunneled-frit will not exceed 20 minutes and can be performed in parallel. Therefore, it is simple and high throughput to fabricate highly reproducible and mechanical stable tunneled frits for capillary columns.

Operation of the Tunneled-Frit Under Ultra High Pressure

As the particle size of the stationary phase is narrowed down from 5 µm to 1.7 µm, higher separation resolution, peak intensity and peak capacity can be achieved to improve the detection sensitivity of trace amount of proteins or peptides in complex mixtures. In the practice of the present invention, we operated a tunneled-frit trap column for nanoLC-MS which used 1.7 µm particles, 25 cm in packed length as the analytical column. To have a flow rate of about 300 nl/min throughout the separation system, we raised the pumping pressure up to 9000 psi. To have such high pressure, ultra high pressure pumps are now available and have been widely used. A low backpressure frit with high mechanical strength for high pressure resistance is needed in nanoUPLC systems. To test the stability of the tunneled-frit under ultra high pressure, the tunneled-frit trap column was packed with 2 cm C18 particles and was connected to the pump by an ultra high pressure micro tight union (UH-432, IDEX Health & Science, Oak Harbor, Wash.) which is able to tolerate pressure up to 15000 psi. At the solvent flow of 50% MeOH, 50 µL/min to build up the pressure of 10,000 psi (maximum pressure test), as shown in FIG. 3, the liquid flow can be sustained more than one week without any particle loss and pressure instability. The stability under such high pressure illustrates that the high physical strength of the tunneled-frit is suitable for ultra high pressure systems and applications such as nano-UPLC-MS for proteomics and UPLC-MS for metabolomics.

Setup for a Tunneled-Frit Trap Column in an Ultra High Pressure System

To equip the trap column for nanoUPLC system, the fittings and ferrules used in the system have to be able to tolerate ultra high pressure. To be able to conveniently replace the trap column, the setup was built as in FIG. 4. In this design, two ultra high pressure micro tight unions (UH-432) were used to connect the trap column. To prevent the peak from broadening, a zero dead volume tee and union were used upstream and downstream of the analytical column separation, respectively. In comparison with the replacement of a commercial trap column, the exchange of the trap column is simple and fast via the movement of peak fittings of micro tight unions without the risk of breaking down the original gold-coated fittings in the switching vale. The liquid leakage in the system can be examined by monitoring the back pressure at a given mobile phase composition and flow rate. If no leakage occurs, the back pressure will stop rising even given more tightening of the fittings. Based on the pumping flow condition of 99% $H_2O$ at 300 nl/min throughout the trap and the analytical column, the pumping pressure can be raised to 800~8400 psi which is the same as in commercial trap column systems.

The Tunneled-Frit Trap Column vs. a Commercial Trap Column

To demonstrate the feasibility for the application of the tunneled-frit for the trap column, enolase digests were analyzed in the nanoUPLC-MS system. Because the same resins were packed in the tunneled-frit trap column and the commercial column and each was separately coupled to the same analytical column, as expected, the mass chromatography was similar for both systems (FIG. 5). However, the retention time was found to have about 1 minute delay, and such could be attributed to the solvent gradient delay due to the spare volume in the trap column (180 µm id, 4 cm of column length, 2 cm of packed length) compared to the commercial trap column (180 µm id, 2 cm of column length, 2 cm of packed length). The tunneled-frit trap column was operated for consecutive runs and the results were compared with the commercial trap column. As shown in Table 1, the peak intensity and peak width for the chosen peaks were similar and is highly reproducible in the run-to-run analysis. In addition, the tunneled-frit columns with frit lengths of about 0.5 mm and about 3 mm were compared in the analysis of peptides and have no observable difference. The RSDs (n=3) of retention time, peak intensity and peak width for peak 1 from column-to-column of tunneled-frit columns were found to be 2.1%, 4.75% and 9.77%, respectively. The high reproducibility in trap column manufactures illustrates the highly practical use of the tunneled-frit trap column in nanoUPLC-MS applications.

TABLE 1

RSDs of retention time, intensity and peak width from run-to-run for the commercial trap column and the tunnel-frit trap column.

| | Time (% RSD) | Intensity (% RSD) | Peak width, FWHM (% RSD) |
|---|---|---|---|
| The tunneled-frit trap column (N = 8) | | | |
| Peak 1 | 15.00 (1.0) | 843 (4.3) | 3.34 (5.6) |
| Peak 2 | 17.42 (1.3) | 858 (5.0) | 4.32 (6.9) |
| Peak 3 | 17.83 (0.5) | 890 (10.0) | 4.35 (2.2) |
| Peak 4 | 20.45 (0.8) | 806 (5.2) | 4.90 (1.8) |

TABLE 1-continued

RSDs of retention time, intensity and peak width from run-to-run
for the commercial trap column and the tunnel-frit trap column.

|  | Time (% RSD) | Intensity (% RSD) | Peak width, FWHM (% RSD) |
|---|---|---|---|
| The Commercial trap column (N = 8) | | | |
| Peak 1 | 13.88 (0.5) | 882 (1.8) | 3.09 (3.5) |
| Peak 2 | 15.59 (0.6) | 721 (5.2) | 4.47 (4.0) |
| Peak 3 | 16.01 (0.7) | 881 (3.5) | 4.29 (2.0) |
| Peak 4 | 18.45 (0.7) | 784 (8.0) | 5.01 (6.0) |

The Performance of the Tunneled-Frit Analytical Column

The ready-made 1.7 μm C18 particles were used as the stationary phase. With the use of a 75 μm id capillary column as an analytical column, a frit with ~15 μm id channel was fabricated by a 15 μm tungsten wire. A short section (~5 mm) of 5 μm particles was first packed and followed by packing 1.7 μm particles to 25 cm in length. As shown in FIG. 6, in comparison with the BEH C18 (1.7 μm, 75 μm×250 mm) analytical column, the similar separation chromatography of enolase digests was obtained in the tunnel-frit analytical column. The separation efficiency was quite similar in compared to the BEH C18 (1.7 μm, 75 μm×250 mm) analytical column (Table 2). The use of 1 mm to 3 mm tunneled frit in length did not show significant influence on separation efficiency. Highly reproducible separation in numerous runs illustrated the stable and robust quality of the tunnel-frit analytical column.

TABLE 2

RSDs of retention time, intensity and peak width from
run-to-run analysis for the commercial analytical
column and the tunnel-frit analytical column.

|  | Time (% RSD), min | Intensity (% RSD) | Peak width, FWHM (% RSD), sec |
|---|---|---|---|
| The commercial analytical column (n = 6) | | | |
| Peak1(708.84) | 17.65(0.87) | 926(7.0) | 4.83(3.7) |
| Peak2(644.84) | 18.18(0.93) | 1136(8.7) | 4.64(3.9) |
| Peak3(643.87) | 20.54(0.34) | 888(6.4) | 5.61(6.7) |
| Peak4(878.43) | 21.55(0.46) | 752(6.9) | 5.09(12.3) |
| The tunnel-frit analytical column (n = 6) | | | |
| Peak1(708.84) | 17.06(0.4) | 1018(7.2) | 5.387(4.9) |
| Peak2(644.84) | 17.51(0.9) | 1150(9.1) | 5.00(5.9) |
| Peak3(643.87) | 19.71(3.1) | 994(10.9) | 5.69(8.7) |
| Peak4(878.43) | 20.685(0.1) | 951(7.3) | 5.35(6.79) |

The Improvement Sensitivity for Phosphopeptide

Because the negatively charged phosphate group of phosphopeptides can interact with metals, this specificity was used to develop the phosphopeptide purification methods such as $TiO_2$ and immobilized metal affinity chromatography (IMAC) techniques. Because the stainless steel frit was used in most of commercial trap columns, a concern arises whether the metal-frit would adsorb the phosphopeptides and reduce the MS signals. Sample of four synthetic phosphopeptides in enolase digests (product No. 186003286, Waters) were tested on commercial trap column and tunneled-frit trap columns. As shown in FIG. 7, phosphopeptide signals were all ratio- nalized to the internal quantitative peak (nonphosphopeptide, 643.9 m/z). In comparison to the commercial trap column, the use of tunnel-frit trap column provides significantly improved phosphopeptide signals with 1.2 (684.8 m/z)~1.7 (432.2 m/z) folds. The use of a non-metal frit in the tunneled frit trap column avoids the phosphopeptide adsorption by the metal-based frit and thus improves the phosphopeptide detection sensitivity.

By using the wire-assisted and sol-gel method, a simple, low back pressure and highly reproducible tunnel frit and methodology were developed. From the results of the tunnel-frit trap column applications, the tunnel-frit trap column can withstand pressure as high as 10,000 psi after packing with 2 cm 5 um resins. In the analysis of protein digests, the results show that tunnel-frit trap column and tunnel-frit analytical columns have similar analytical results compared with commercial system. The on column frit preparation method, resulting tunneled fit, and UPLC applications are novel and unobvious. The application of the tunnel frit in nanoUPLC-MS yields substantial cost reduction, for example, in proteomics labs for trap and analytical columns and also improves the sensitivity for phosphopeptides. The tunnel frit methods and means are also suitable to be widely applied to other packed columns for chromatography enrichment and separation applications.

The foregoing description of the invention and the figures and tables contained herein and the legends thereof illustrate and describe embodiments of the present invention. It is to be understood that the invention is capable of use in various other combinations, modifications, and environments and is capable of changes or modifications within the scope of the inventive concept as expressed herein, commensurate with the teachings herein and/or the skill or knowledge of the relevant art. The embodiments described herein are further intended to explain best modes known of practicing the invention and to enable others skilled in the art to utilize the invention in such, or other, embodiments and with the various modifications required by the particular applications or uses of the invention. Accordingly, the description is not intended to limit the invention to the form or application disclosed herein. All references and publications cited herein are hereby incorporated by reference.

What is claimed is:

1. The combination of a capillary column adapted to retain a stationary packing and a tunneled fit adhered to the column at one end thereof, the combination being suitable for use in a liquid chromatography (LC) and in capillary electrophoresis chromatography systems and for nanoflow and microflow operations, wherein said tunneled fit contains a tunnel in open communication between the inside and outside of said column, and wherein the tunnel is not sealed while under pressures of up 12,000 psi when performing the LC, capillary electrophoresis chromatography, and nanoflow and microflow operations, and wherein the tunneled fit is made by the process of:
   providing a capillary column;
   inserting a heat resistant wire a predetermined distance into said column;
   contacting said column with an uncured material capable of bonding to the column and causing the uncured material to penetrate into the column not further than the depth of the wire;
   removing the wire when the uncured material is set; then further curing the material to create a high pressure resistant bond of the resulting tunneled frit and the column.

2. The combination of claim 1 wherein said tunneled fit is formed in place in said column and cured so as to form a durable bond capable of withstanding ultra high pressure.

3. The combination of claim 2 wherein said ultra high pressure is up to about 12,000 psi.

4. The combination of claim 1 wherein said tunneled fit comprises dense silica glass and other polymerized materials.

5. The combination of claim 1 wherein the ratio of the diameter of the tunnel to the diameter of the frit is between about 0.070 and about 0.080 to about 0.25 and about 0.35.

6. The combination of claim 1 wherein said column contains a stationary packing.

7. The combination of claim 1, wherein the liquid chromatography is ultra high pressure liquid chromatography.

8. A method of separating proteinaceous material for analysis which comprises passing a protein containing material at elevated pressure through the combination of claim 1.

* * * * *